United States Patent
Smith et al.

(10) Patent No.: US 6,869,796 B2
(45) Date of Patent: Mar. 22, 2005

(54) METHOD OF INTRODUCING ORGANIC MOLECULES INTO TARGET CELLS

(75) Inventors: Edvard Smith, Hagersten (SE); Lars Branden, Stockholm (SE)

(73) Assignee: Avaris AB, Stockholm (SE)

( * ) Notice: Subject to any disclaimer, the term of this patent is extended or adjusted under 35 U.S.C. 154(b) by 514 days.

(21) Appl. No.: 09/874,270

(22) Filed: Jun. 6, 2001

(65) Prior Publication Data

US 2002/0031830 A1 Mar. 14, 2002

Related U.S. Application Data

(63) Continuation-in-part of application No. 09/486,398, filed as application No. PCT/SE98/01527 on Aug. 26, 1998, now abandoned.

(30) Foreign Application Priority Data

Aug. 26, 1997 (SE) ............................................... 9703073

(51) Int. Cl.$^7$ .............................................. C12N 15/86
(52) U.S. Cl. .................... 435/456; 435/325; 435/372
(58) Field of Search ............................... 435/456, 325, 435/372

(56) References Cited

U.S. PATENT DOCUMENTS 5,252,216 A * 10/1993 Folena-Wasserman et al. .. 210/635

OTHER PUBLICATIONS

K. Krishna Mohan et al., *Conceptual Design of a Cellular Filter to Remove Trace Viral Contaminants in Blood*, publ. Biotechnol. Prog., 1990, pp. 104–113.

* cited by examiner

*Primary Examiner*—James Ketter
(74) *Attorney, Agent, or Firm*—Young & Thompson

(57) ABSTRACT

The present invention relates to a method of introducing organic molecules carrying genetic information into isolated target cells, which comprises the step of passing a supernatant comprising said organic molecules through a fluidized collection of said target cells during an essentially constant flow. The fluidisation is provided by directing a flow of the supernatant so as to essentially counteract the gravitational force of the target cells, or alternatively a force applied thereon. Thus, the present method enables an efficient introduction of genetic information into the target cells.

16 Claims, 7 Drawing Sheets

Figure 2
○ : Cell
● : Virus
↓ : Flow Direction
-- : Filter / Support
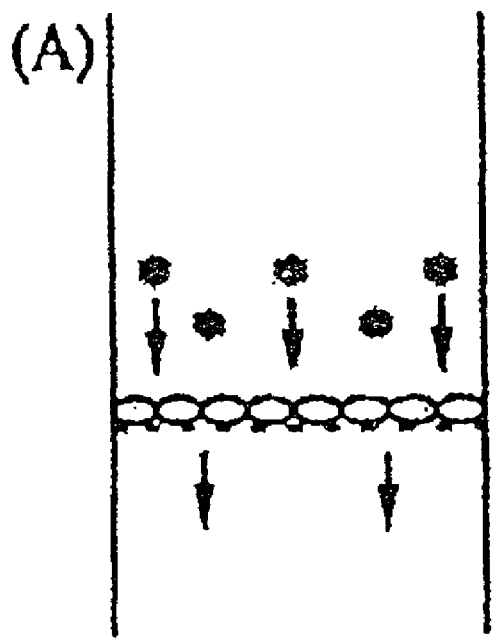
(A)
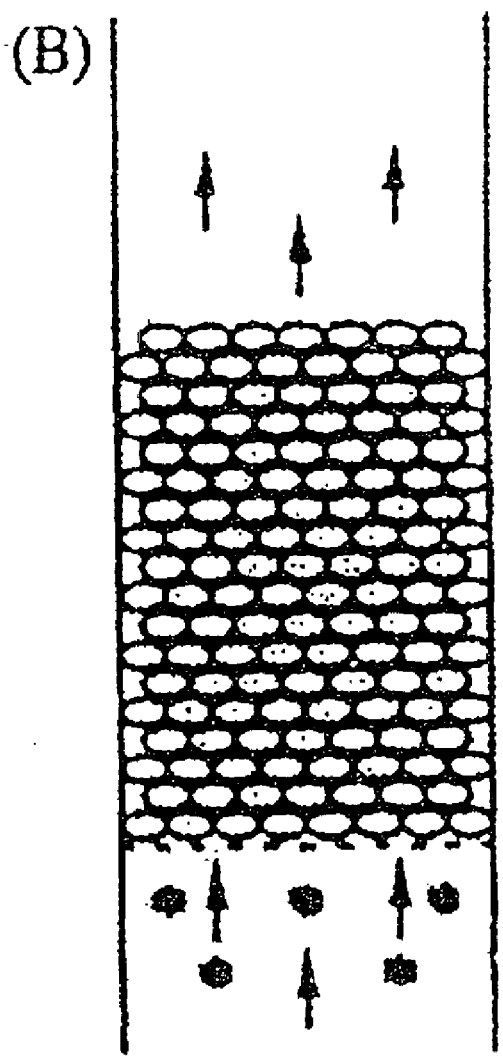
(B)

METHOD OF INTRODUCING ORGANIC MOLECULES INTO TARGET CELLS

This application is a continuation-in-part of prior application Ser. No. 09/486,398, filed Mar. 30, 2000, now abandoned which is a national stage of PCT/SE98/01527, filed Aug. 26, 1998, which claimed priority of Swedish application No. 9703073-8, filed Aug. 26, 1997.

FIELD OF THE INVENTION

The present invention relates to a method of introducing organic molecules into target cells, which comprises the step of passing a supernatant comprising said organic molecules through a collection of said target cells. In addition, the present invention also relates to a system especially adapted for performing the method according to the invention.

BACKGROUND AND PRIOR ART

Since the discovery of the DNA molecules by Watson and Crick in the 50's, huge scientific progress has been made within the field of biochemistry and biology. Recombinant DNA techniques and techniques for genetic manipulation are continuously developped based on the new discoveries and new medical applications thereof are proposed every day. In general, such methods are based on the principle that some kind of genetic information containing material, such as a gene, is transferred from its original and native environment to a new environment, where some desired properties thereof may be utilized in a new context. Usually, some kind of carrier or vector is used for such a transfer procedure, of which one example is virus. Viruses are due to the native properties thereof capable of infecting cells and thereby transferring its own contents of nucleic acids thereto. Successful genetic manipulation requires appropriate reagents, such as vectors, as well as practical and effective procedures for the performance thereof. As one example of a medicinal application, which is of utmost interest at the moment, may gene therapy be mentioned. In gene therapy, vectors, such as virus particles, are used to introduce nucleic acid sequences in receptor cells, where said sequences may compensate for damages or mutations, or even correct mutations, in the native genes of said cells.

During the elaboration of better and more efficient recombinant techniques, it has appeared that the cells which are desirable as receptor or target cells often are quite difficult to infect. The simplest and most straight forward approach to enhance the number of infected cells is to increase the amount of virus used during the infection procedure, whereby the number of completed infection occurences in receptor cells hopefully increase as well. The result of this approach is, however, an increased demand for cells producing virus in high concentrations. Problems arise, however, when cells are to produce large amounts of a virus. In many cases, the virus is toxic to the producer cells when present in such massive amounts, and, accordingly, the cells are killed when the virus production is increased. In cases where large foreign nucleic acid sequences have been introduced in the virus, the virus particles may not be assembled in a correct way during a large scale production.

Different ways of transfecting cells with vectors, such as viruses, have been proposed. One procedure is disclosed, where a suspension of target cells is held in a container, whereafter a virus containing cell medium is added thereto. However, since a virus is a colloidal particle, it will move randomly with Brownian motions in a liquid. Accordingly, the transfection takes place randomly in such a procedure, depending on the amount of particles that eventually hit the cells. Only a small fraction of the virus particles will ever reach contact with target cells and, in addition, the contact area and binding achieved is usually too loose to permit a sufficient transfection. The virus containing cell suspension may be stirred or agitated in order to increase the efficacy of such a process. Still, the efficiency of the process is low and not optimal for an industrial method.

In order to increase the contact area between target cells and virus, and thus increase the number of infection occurences, target cells have been immobilized on membranes. Then, a virus containing supernatant is passed through the membrane. Indeed, a better contact between virus particles and cells than in the case described above may be obtained. However, such a membrane technique will exhibit other essential drawbacks. One problem when using a membrane in connection with cells is that it will sooner or later be obstructed by clogging cells. Thus, the life-time of such a membrane and also the possible choices of flow conditions are limited. Another problem results from the fact, that the virus containing supernatant must be forced against the target cells on the solid membrane, whereupon the virus binding receptors on the target cells are often damaged. Consequently, the possible binding of virus theron will be reduced. An additional drawback with the membrane techniques originates from the fact that only a limited number of cells may be immobilized on each membrane, which number is restricted by the area of the membrane. In fact, preliminary calculations reveal that to attain a sufficiently large amount of cells for clinical experiments the diameter of such a membrane need to be about 34 m. In addition, the amount of supernatant needed to wet such an area is enormous. Naturally, such a large membrane is hardly applicable in practice.

Other cellular filters have been proposed for similar applications. In Biotechnol. Prog. 1990, 6, p. 104–113, by Krishna Mohan et al, a cellular filter is disclosed for the removal of trace viral contaminants in blood. However, the aim of these authors is to purify blood or similar fluids, and therefore, the properties of the resulting fluid are stressed, while no particular account is taken to protect or enhance the cells that absorb the virus. In this publication, one strategy is disclosed, where cells are grown on microcarriers and stabilized by a cross-linking agent. Consequently, a cellular filter is accomplished. Said filter will exhibit properties similar to the above described membranes with immobilized cells thereon, i.e. it will constitute an almost stable element against which cells absorbing virus will be forced. Another strategy disclosed in this article involves the use of clusters or aggregates of cells around microcarriers. The microspheres used to cluster the cells exhibits a magnetic nature, which is then utilized combined with other magnetic equipment around the reaction vessel. Obviously, such a magnetic agitation will be efficient for the application disclosed in the article, i.e. the recovery of a virus free solution. However, in the instance when the infected cells are the products to be used for later applications, it will result in too large a cell desintagration and, in addition, the magnetic field may be harmful as regards internal properties of the absorbing cells.

SUMMARY OF THE INVENTION

The object of the present invention is to solve one or more of the problems above. Accordingly, the present invention relates to a method of introducing at least one organic molecule into one or more isolated target cells, which comprises the step of passing a supernatant comprising organic molecules through a collection of free floating target cells. Thereby, the organic molecules can efficiently be introduced into the target cells. Another object of the invention is a cell which has been genetically manipulated by introduction therein of an organic molecule by the method according to the invention. A last aspect of the invention is a system especially suited for performing the claimed method. More specifically, the objects of the invention are solved as defined in the appended claims.

BRIEF DESCRIPTION OF THE DRAWINGS

FIG. 2 shows a schematical comparison between (A) a prior art flow-through transduction and (B) reversed flow-through transduction according to the invention.

DEFINITIONS

Figure 1:
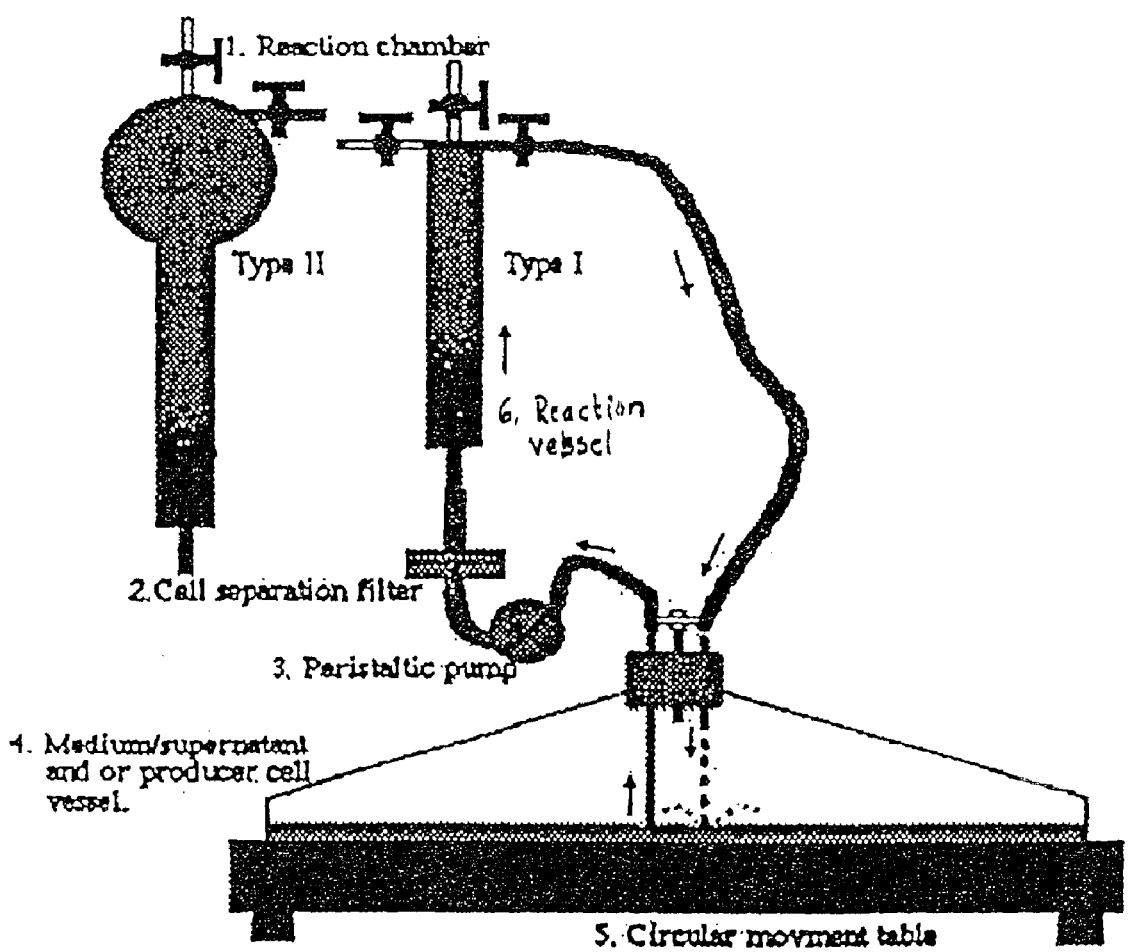
FIG. 1 shows an illustrative system (Type I) for performing the method according to the invention including a reaction vessel 1; a cell separation filter 2; a peristaltic pump 3; a producer vessel 4; a circular movement table 5; and a reaction vessel 6.

In the present application, the term "organic molecule" refers to a biomolecule which can be transferred from one biological entity to another. An "organic entity" as used herein is also capable of providing genetic information and can e.g. be a DNA, even though several other examples will be discussed in the detailed description below.

The terms "isolated" means biologically pure, i.e. the term refers to material which is substantially or essentially free from components which normally accompany it as found in its native state.

The term "target cell" relates to any cell line which can be maintained in a suitable medium in a column and which is capable of taking up i.e. allowing entrance to one or more organic molecules.

The term "a particle comprising organic molecules" refers to a biological entity which contains the above described biomolecule and can e.g. be exampified by a virus.

"Gene transfer" refers to methods or systems for reliably inserting DNA of interest into a target cell. Such methods can result in transient expression of non-integrated transferred DNA, extrachromosomal replication and expression of transferred replicons (e.g., episomes), or integration of transferred genetic material into the genomic DNA of target cells. A cell which has been "genetically modified" has been transfected or transduced, either in vivo or in vitro, with a gene transfer vector containing a DNA molecule of interest.

The term "transfection" is used to refer to the uptake of foreign DNA by a cell. A cell has been "transfected" when exogenous DNA has been introduced inside the cell membrane. A number of transfection techniques are generally known in the art. See, e.g., Graham et al. (1973) Virology, 52:456, Sambrook et al. (1989) Molecular Cloning, a laboratory manual, Cold Spring Harbor Laboratories, New York, Davis et al. (1986) Basic Methods in Molecular Biology, Elsevier, and Chu et al. (1981) Gene 13:197. Such techniques can be used to introduce one or more exogenous DNA moieties into suitable host cells. The term refers to both stable and transient uptake of the genetic material, and includes uptake of peptide- or antibody-linked DNAs.

The term "transduction" denotes the delivery of a DNA molecule to a target cell either in vivo or in vitro, via a replication-defective viral vector, such as a retroviral gene transfer vector.

By "vector" is meant any nucleic acid construct capable of directing the expression of a gene of interest and which can transfer gene sequences to target cells. Thus, the term includes cloning and expression vehicles, as well as viral vectors.

A "coding sequence" or a sequence which "encodes" a selected molecule, is a nucleic acid molecule which is transcribed (in the case of DNA) and translated (in the case of mRNA) into a polypeptide in vivo when placed under the control of appropriate regulatory sequences.

A "nucleic acid molecule," or "nucleotide sequence" can include, but is not limited to, procaryotic sequences, eucaryotic mRNA, cDNA from eucaryotic mRNA, genomic DNA sequences from eucaryotic (e.g., mammalian) DNA, and even synthetic DNA sequences. The term also captures sequences that include any of the known base analogs of DNA and RNA.

DETAILED DESCRIPTION OF THE INVENTION

More specifically, the present invention relates in a first aspect to a method of introducing at least one organic molecule into one or more target cells comprising the passage of a supernatant, wherein the organic molecules are originally maintained, through a collection of target cells, which method comprises the steps of (a) providing isolated target cells in a reaction vessel, which target cells are capable of allowing entrance or actively taking up organic molecules;

(b) providing a supernatant containing organic molecules; and (c) contacting the organic molecules with the target cells by passing the supernatant through the reaction vessel so as to provide a fluidized or semi-fluidized bed of target cells in the reaction vessel, wherein the flow of supernatant through the reaction vessel is controlled to provide an essentially constant flow between fluidized target cells and organic molecules allowing a sufficient contact area and time therebetween to enable organic molecules to enter target cells. The present invention shows for the first time that such free floating target cells maximize the possibilities for interaction of the organic molecule to its cognate site on the target cell.

The flow of the supernatant is controlled to provide essentially constant flow conditions between supernatant comprising organic molecules and target cells floating free in a solution or suspension. As used herein, the term "essentially constant flow" should be interpreted as a flow, which is constant over a period of time, while allowing shorter periods of intermittent flow therein. Thus, the flow of the supernatant is controlled to provide a sufficiently close contact, as regards both contact time and area, between the organic molecules and the target cells, to enable the organic molecules to be introduced efficiently into the target cells. In order to set a sufficient value of the flow, samples of target cells may be withdrawn from the reaction vessel and analyzed as regards whether the organic molecules in question have been introduced therein or not. Such methods are well known and protocols for routine procedures are easily found in the literature. Thus, such testing or analysis is easily performed by the skilled person in this field. The supernatant can be any liquid which is suitable for the organic molecule and target cells and can accordingly be a conventional growth media or simply a bufered aqueous solution, such as a saline bufered phosphate solution.

The target cells may be any procaryotic or eucaryotic cells and they may be of human or animal origin. More specifically, according to the present invention, the target cell is selected so as to exhibit a sufficient binding capacity to each respective organic molecule. In other words, in the present method, it will not be required to force the organic molecule to enter the target cell.

Examples of target cells are primary cells taken from a donor, a cell line, such as a mammalian cell line, hematopoietic stem cells, such as such as $CD34^+$ stem cells, T-cells, hepatic cells, embryonic stem cells, immortalized cell lines, etc. Target cells can be used free or immobilized on suitable microcarriers, as discussed in more detail below. In one embodiment, the target cells are clonal cells.

Thus, in one embodiment, an immortalized cell line is used as a target cell. Normal cells can be immortalized, that is to say made capable of multiplying indefinitely. Indeed, normal cells do not survive more than a ten passages. For that, techniques for the transfection of cells, with the aid of specially adapted vectors, such as the SV40 vector comprising a sequence of the large T antigen (R. D. Berry et al., Br. J. Cancer, 57, 287–289, 1988), or a vector comprising DNA sequences of the human papillomavirus (U.S. Pat. No. 5,376,542), are generally used. As a further example, Sanderson et al. have immortalized normal cells of the foetal small intestine (Int. Arch. Allergy Immunol., 107, 396–397, 1995).

In an advantageous embodiment, the target cells are stem cells. Stem cells are advantageously used in gene therapy contexts since they can be differentiated into other cell types in vitro and can be isolated using known methods. For example, in mice, bone marrow cells are isolated by sacrificing the mouse and cutting the leg bones with a pair of scissors. Stem cells are isolated from bone marrow cells by panning the bone marrow cells with antibodies which bind unwanted cells, such as $CD4^+$ and $CD8^+$ (T cells), $CD45^+$ (panB cells), GR-1 (granulocytes) and $Ia^d$ (differentiated antigen presenting cells). For an example of this protocol, see Inaba et al. (1992) J. Exp. Med. 176:1693–1702. In humans, stem cells can be isolated by bone marrow aspirations from iliac crests e.g. under general anesthesia in the operating room. The bone marrow aspirations are approximately 1,000 ml in quantity and are collected from the posterior iliac bones and crests. Human hematopietic progenitor and stem cells are characterised by the presence of a CD34 surface membrane antigen. This antigen is useful for its purification, e.g. on affinity columns which bind CD34. In this context, see e.g. Ho et al., Stem Cells 13 (suppl. 3): 100–105; or Brenner (1993) Journal of Hematotherapy 2:7–17. For isolation of stem cells from fetal cord blood, see e.g. Yu et al. (1995) Proc. Natl. Acad. Sci. USA 92:699–703.

Other cells can be isolated by the skilled in this field using similar techniques and used as target cells in the present method.

Figure 4:
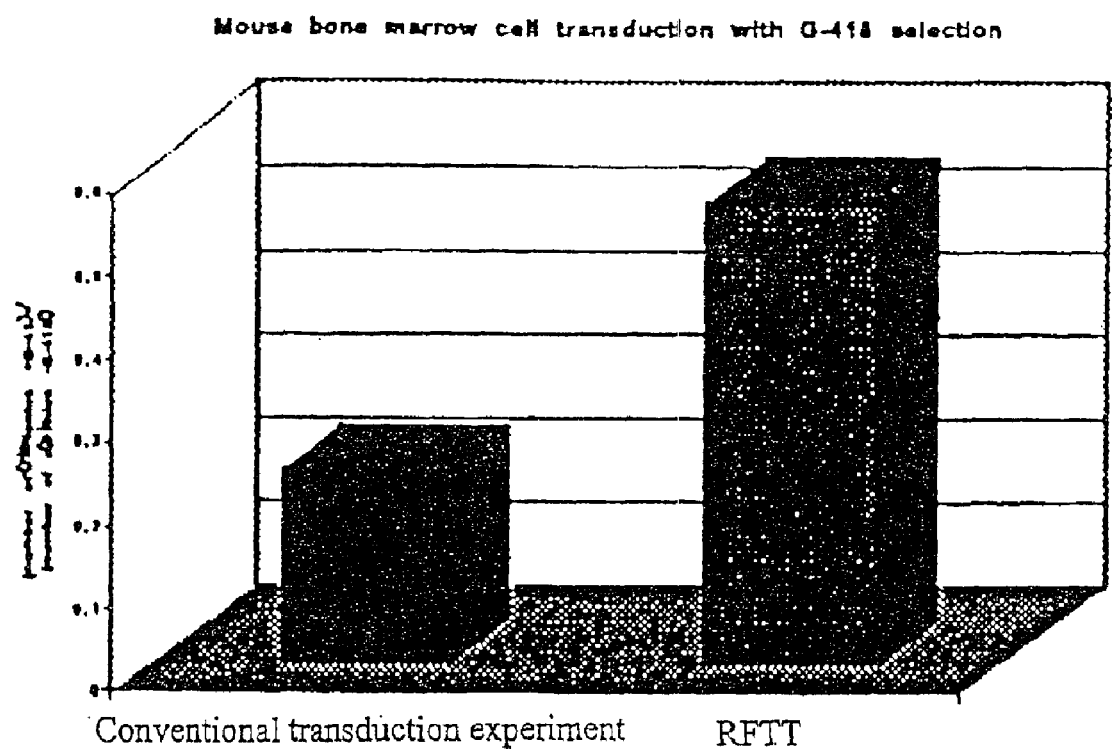
FIG. 4 shows the results of transduction according to the present invention of murine bone marrow cells with a maloney leukemia virus vector containing the neo selection marker as compared to a conventional experiment.
Figure 6:
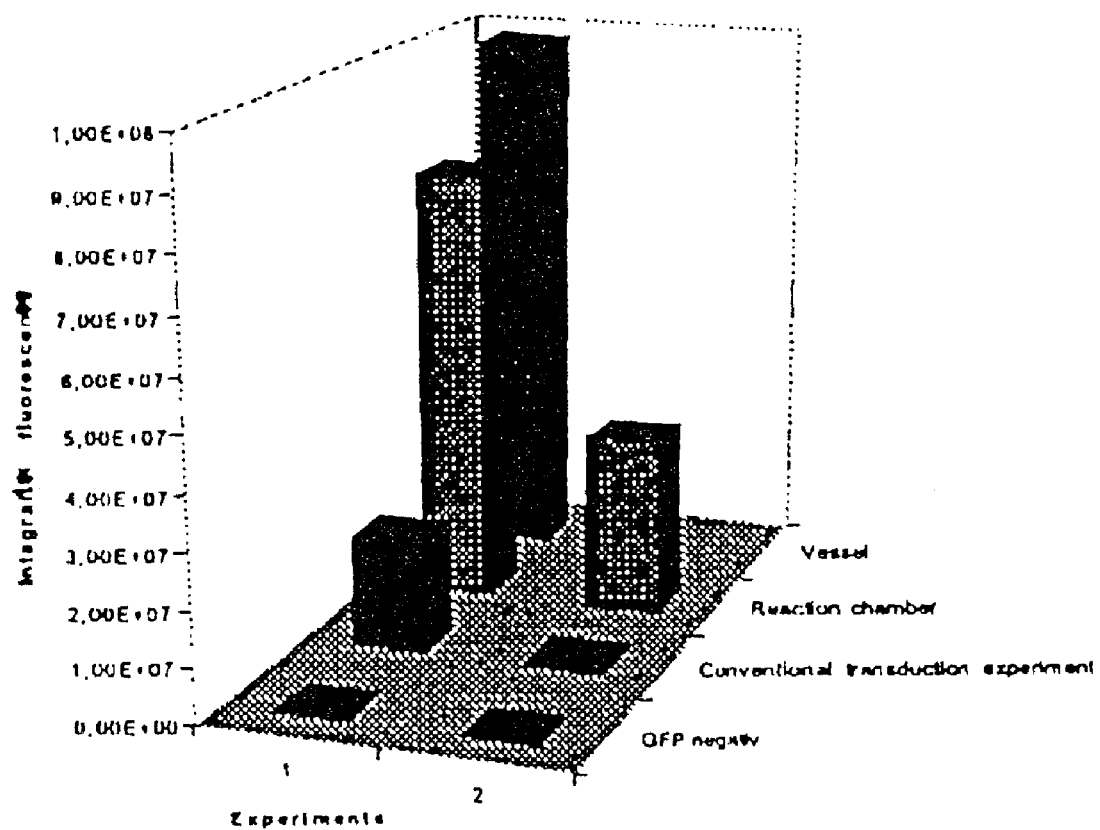
FIG. 6 shows the integrated fluorescence measured from the images in FIG. 5.

The concept of the reverse flow through transduction (RFTT) according to the invention is to minimize cell stress and to have optimal conditions for organic molecule uptake in order to achieve a maximal viral adsorption or transfection. Data illustrating the superior results obtained by the present invention is shown in FIG. 4 and FIG. 6 and will be discussed in more detail below.

In a preferred embodiment of the present method, the flow is achieved by providing a direction of the flow of supernatant which essentially counteracts the gravitational force, or any suitable multiplicity thereof, of the target cells. Thus, the flow will be set at a value, which inter alia depends on the weight of, or pressure caused by, the isolated target cells, so that a stable and constant flow is achieved. The supernatant according to the present invention is most preferably passed through the target cells from below, so as to counteract the pressure or weight of the target cells. Accordingly, in an advantageous embodiment, the method according to the invention is performed during conditions similar to a fluidized bed, where essentially free floating target cells in a solution or suspension comprise the bed.

In alternative embodiments of the present method, a centrifugal force may be applied on the target cells and used instead of the gravitational force used as above, in which case the supernatant is passed through the target cells in a direction, which essentially counteracts said centrifugal force. As a person skilled in this area easily realizes, there exist several different possibilities and embodiments of the herein exemplified concept of allowing a supernatant to counteract the gravitational or centrifugal force of target cells, all of which are encompassed by the claims defining the present invention.

In addition to the above defined advantageous contact area and time, another advantage of the method according to the invention is, that depending on the specific relation between the supernatant and the weight of the target cells according to the invention, the supernatant comprising organic molecules will apply a certain pressure on the target cells. This pressure will improve the contact between target cell-organic molecule at the target cell surface, thereby further enhancing the process of introducing organic molecules therein. Naturally, said pressure will not be as high as to damage or desintegrate the target cells. Since the target cells are floating free in a suspension or solution during the method according to the invention, there will be no solid member onto which the target cells may be forced, and thereby damaged. Thus, the pressure will enhance the introduction of organic molecules without unnecessary damage on the target cells. Contrary, in the prior art methods, target cells have been forced towards solid membranes or filters by a liquid flow. Such solid membranes or filters are in addition easily clogged and accordingly blocked after use during a certain period of time. In summary, the problems of desintegration of cells due to an applied pressure onto a solid member is eliminated by the method according to the present invention, wherein the floating target cells themselves comprise the only filter used. In addition to this, the method according to the invention may be used as a continuous process during a virtually unlimited period of time, as no filter clogging can occur.

Accordingly, the method according to the present invention is advantageously used in the context of fragile cells, which otherwise might be impaired by membranes or solid filters used in the prior art methods for introduction of organic molecules.

The constant flow conditions in the method according to the invention are easily set at flow rates suitable for each specific case, depending on both the kind of target cells and the organic material to be introduced therein, or transferred thereto.

In one advantageous embodiment of the present invention, the same supernatant is passed several times through the target cells (recirculated). Such a recirculation procedure will increase the total number of target cells, which take up organic molecules to become genetically modified, recombinant cells, and thus will increase the efficacy of the process. Obviously, the recirculation according to the invention is not comparable to a recirculation over a membrane with immobilized cells according to the prior art, as a membrane will eventually be occluded by particles, which limits the number of times recirculation is possible.

In one particular embodiment of the method according to the present invention, the target cells are immobilized on small carriers capable of being fluidized, such as microcarriers. However, said microcarriers are still floating free in the suspension, whereby the same advantages as described above with free floating cells are achieved. This embodiment differs from the strategy disclosed in the previously mentioned article from Biotechnol. Prog, 1990, 6, p 104–113, by the fact that according to the invention, the microcarriers are floating free, as in a fluidized bed, while the microcarriers disclosed in said article are cross-linked and thereby stabilized. Whether it is more advantageous to immobilize the target cells on microcarriers or to use target cells free in a suspension or a solution is easily determined by a person skilled in the art, depending on the kind of target cells, organic molecules as well as other materials and parameters.

A specific embodiment of the present invention is a method of introducing at least one organic molecule into one or more target cells, which comprises the step of passing a supernatant, wherein the organic molecules has been originally maintained within particles, through a colection of target cells. In the present context, it is to be understood that the term "originally maintained" means that the organic molecule is present in the particle up to the point of time, when said particle by an interaction with the target cell surface transfers the organic molecule into the target cell. The target cells can as above be isolated cloned cells present in a suspension or solution.

The particles can be any particle, in the form of a carrier or a vector, capable of interaction with target cells and capable of harbouring an organic molecule or biomolecule which carries genetic information in some form. In this context, "interaction" means a contact to the extent necessary for allowing an organic molecule, such as a nucleic acid, to exit the particle and enter the target cell e.g. via a receptor, which interaction can be a binding. As a specific example, the sugar lactose can be mentioned. Hepatocytes express a receptor called asialoglycoprotein receptor. This receptor binds lactose very efficiently. Thus, by linking lactose to an organic molecule this ability to take up lactose can be utilzed to stimulate the uptake of the conjugated organic molecule. Accordingly, in a specific embodiment, the present method utilises an organic molecule conjugated to lactose to transfer said organic molecule to hepatocytic target cells. The same principle can be utilised to conjugate an organic molecule to an entity for which a specific receptor is known, and use the conjugate in combination with a target cell that express that receptor.

More specifically, the particles may be native viruses or viruses, wherein a genetic sequence, such as a marker sequence or a therapy gene, has been introduced by a recombinant technique. Thanks to the advantageous contact area and time between target cells and the particles containing organic molecules, the method according to the invention is especially suitable for the case where the herein defined introduction is a transfection of genetic information from a rapidly degrading virus. For example, retrovirus (Miller, Nature 357:455–460 (1992)) are e.g. degraded as rapidly as 50% in 8 h. Accordingly, such viruses will need to rapidly hit the target cells, bind thereto and infect them. Alternatively, the particle may be any other kind of carrier commonly used in techniques for genetic manipulation or especially designed for a particular purpose, see e.g. the references given below. For a review of general principles relating to the specific example wherein virus is used as the particle to transfer genetic information into stem cells, see e.g. Anderson, W. F. (1992) Science, 256: 808–813; Miller, A. D. (1992) Nature, 357: 455–460. The retrovirus can e.g. be a leukemia virus such as a Moloney Murine Leukemia Virus (MMLV), the Human Immunodeficiency Virus (HIV), or the Gibbon Ape Leukemia virus (GALV). Further examples of particles according to the invention is adenovirus, lentivirus, In general, target cells which are able to absorb, or bind to, other cells or particles, exhibit the receptors for that purpose on their surfaces. Accordingly, practically all such receptors on the target cells surfaces, to which organic molecules can bind, will be exposed to the supernatant and the organic molecules therein. As compared to the prior art techniques, this feature of the present invention will increase the number of bound particles as well as the binding rate and thus enhance the efficacy of the introduction of organic molecules from the particles into target cells.

In its broadest scope, the method according to the present invention may use any organic molecules capable of interaction, directly or indirectly, with target cells. The organic molecules may be any biomolecules, inter alia nucleic acids, complexes of nucleic acids with liposomes, preferably cationic liposomes, such as complexes suitable for use in liposomal transfection procedures, other complexes, or genetic information originating from virus, such as DNA or RNA, coding sequences etc. Methods to form liposomes are known in the art, see e.g. Prescott, Ed., Methods in Cell Biology, Volume XIV, Academic Press, New York, N.Y. (1976). The organic molecules may be native, produced by recombinant DNA techniques or synthetically produced, such as by organic synthesis or peptide synthesis.

In one embodiment, the organic molecules are present in the supernatant within particles, such as DNA or RNA within a viral particle. The expression "particles containing organic molecules" as used herein may refer to one molecule such as a peptide or protein, which thus constitutes the particle referred to herein as well as the organic molecule, in one single element. The organic molecules used in the method according to the invention may be molecules containing some kind of genetic information, such as DNA or RNA present in a virus particle. Thus, the method of introducing organic molecules according to the invention may, for example, be a transfection process, where it is desired to transfer genetic information from a vector, such as a virus particle, into a target cell.

The general considerations and conditions in view of gene transfer are known to those of skill in this field and have been discussed extensively in the literature. For viral transfer, see for example Douglas J T, Curiel D T. Strategies to accomplish targeted gene delivery to muscle cells employing tropism-modified adenoviral vectors. Neuromuscul Disord. 1997 July;7(5):284–98. Review. PMID: 9267842; UI: 97413199; Stevenson S C, Rollence M, Marshall-Neff J, McClelland A. Selective targeting of human cells by a chimeric adenovirus vector containing a modified fiber protein. J Virol. 1997 June;71(6):4782–90. PMID: 9151872; UI: 97296288; Krasnykh V N, Mikheeva G V, Douglas J T, Curiel D T. Generation of recombinant adenovirus vectors with modified fibers for altering viral tropism. J Virol. 1996 October;70(10):6839–46. PMID: 8794325; UI: 96386575; Wickham T J, Segal D M, Roelvink P W, Carrion M E, Lizonova A, Lee G M, Kovesdi I. Targeted adenovirus gene transfer to endothelial and smooth muscle cells by using bispecific antibodies. J Virol. 1996 October;70(10):6831–8. PMID: 8794324; UI: 96386574; Mikawa T. Retroviral targeting of FGF and FGFR in cardiomyocytes and coronary vascular cells during heart development. Ann N Y Acad Sci. 1995 Mar. 27;752:506–16. Review. No abstract available. PMID: 7755295; UI: 95274942; Su Y, Popik W, Pitha P M. Inhibition of human immunodeficiency virus type 1 replication by a Tat-activated, transduced interferon gene: targeted expression to human immunodeficiency virus type 1-infected cells. J Virol. 1995January;69(1):110–21. PMID: 7983701; UI: 95074854; Douar A M, Adebakin S, Themis M, Pavirani A, Cook T, Coutelle C. Foetal gene delivery in mice by intra-amniotic administration of retroviral producer cells and adenovirus. Gene Ther. 1997 September;4(9):883–90. PMID: 9349424; UI: 98010137; Hansen J E, Gram G J, Nielsen S D, Sorensen A, Jensen P B, Sehested M, Nielsen; J O, Rorth M. Transduction potential of human retroviruses in highly proliferating small-cell lung cancer cells as well as non-proliferating hematopoietic stem cells. APMIS. 1997 September;105(9):723–9. PMID: 9350217; UI: 98011292; Lozier J N, Yankaskas J R, Ramsey W J, Chen L, Berschneider H, Morgan R A. Gut epithelial cells as targets for gene therapy of hemophilia. Hum Gene Ther. 1997 Aug. 10;8(12):1481–90. PMID: 9287148; UI: 97431643; Zhou W, Resh M D. Differential membrane binding of the human immunodeficiency virus type 1 matrix protein. J Virol. 1996 December;70(12):8540–8. PMID: 8970978; UI: 97126054; Hurford R K Jr, Dranoff G, Mulligan R C, Tepper R I. Gene therapy of metastatic cancer by in vivo retroviral gene targeting. Nat Genet. 1995 August;10(4):430–5. PMID: 7670493; UI: 95400324; Miller N, Vile R. Targeted vectors for gene therapy. FASEB J. 1995February;9(2): 190–9. Review. PMID: 7781922; UI: 95301122; Roberts M R, Qin L, Zhang D, Smith D H, Tran A C, Dull T J, Groopman J E, Capon D J, Bym R A, Finer M H. Targeting of human immunodeficiency viris-infected cells by CD8+ T lymphocytes armed with universal T-cell receptors. Blood. 1994 Nov. 1;84(9):2878–89. PMID: 7949163; UI: 95036321; Kato K, Yoshida J, Mizuno M, Sugita K, Emi N. Retroviral transfer of herpes simplex thymidine kinase gene into glioma cells causes targeting of gancyclovir cytotoxic effect. Neurol Med Chir (Tokyo). 1994 June;34(6):339–44. PMID: 7523964; UI: 95022006.

Furthermore, for a general reference to the principles and conditions for non-viral gene transfer, see e.g.Douglas J T, Curiel D T. Strategies to accomplish targeted gene delivery to muscle cells employing tropism-modified adenoviral vectors. Neuromuscul Disord. 1997 July;7(5):284–98. Review. PMID: 9267842; UI: 97413199; Stevenson SC, Rollence M, Marshall-Neff J, McClelland A. Selective targeting of human cells by a chimeric adenovirus vector containing a modified fiber protein. J Virol. 1997 June;71(6):4782–90. PMID: 9151872; UI: 97296288; Krasnykh V N, Mikheeva G V, Douglas J T, Curiel D T. Generation of recombinant adenovirus vectors with modified fibers for altering viral tropism. J Virol. 1996 October;70(10):6839–46. PMID: 8794325; UI: 96386575; Wickham T J, Segal D M, Roelvink P W, Carrion M E, Lizonova A, Lee G M, Kovesdi I. Targeted adenovirus gene transfer to endothelial and smooth muscle cells by using bispecific antibodies. J Virol. 1996 October;70(10):6831–8. PMID: 8794324; UI: 96386574; Mikawa T.

Retroviral targeting of FGF and FGFR in cardiomyocytes and coronary vascular cells during heart development. Ann N Y Acad Sci. 1995 Mar. 27;752:506–16. Review. No abstract available. PMID: 7755295; UI: 95274942; Su Y, Popik W, Pitha P M. Inhibition of human immunodeficiency virus type 1 replication by a Tat-activated, transduced interferon gene: targeted expression to human immunodeficiency virus type 1-infected cells. J Virol. 1995 January;69(1):110–21. PMID: 7983701; UI: 95074854; Douar A M, Adebakin S, Themis M, Pavirani A, Cook T, Coutelle C. Foetal gene delivery in mice by intra-amniotic administration of retroviral producer cells and adenovirus.

Gene Ther. 1997 September;4(9):883–90. PMID: 9349424; UI: 98010137; Hansen J E, Gram G J, Nielsen S D, Sorensen A, Jensen P B, Sehested M, Nielsen J O, Rorth M. Transduction potential of human retroviruses in highly proliferating small-cell lung cancer cells as well as non-proliferating hematopoietic stem cells. APMIS. 1997 September; 105(9):723–9. PMID: 9350217; UI: 98011292; Lozier J N, Yankaskas J R, Ramsey W J, Chen L, Berschneider H, Morgan R A. Gut epithelial cells as targets for gene therapy of hemophilia. Hum Gene Ther. 1997 Aug. 10;8(12):1481–90. PMID: 9287148; UI: 97431643; Zhou W, Resh M D. Differential membrane binding of the human immunodeficiency virus type 1 matrix protein. J Virol. 1996 December;70(12):8540–8. PMID: 8970978; UI: 97126054; Hurford R K Jr, Dranoff G, Mulligan R C, Tepper R I. Gene therapy of metastatic cancer by in vivo retroviral gene targeting. Nat Genet. 1995 August;10(4):430–5. PMID: 7670493; UI: 95400324; Miller N, Vile R. Targeted vectors for gene therapy. FASEB J. 1995 February;9(2):190–9. Review. PMID: 7781922; UI: 95301122; Roberts MR, Qin L, Zhang D, Smith D H, Tran A C, Dull T J, Groopman J E, Capon D J, Bym R A, Finer M H. Targeting of human immunodeficiency virus-infected cells by CD8+ T lymphocytes armed with universal T-cell receptors. Blood. 1994 Nov. 1;84(9):2878–89.

PMID: 7949163; UI: 95036321; Kato K, Yoshida J, Mizuno M, Sugita K, Emi N. Retroviral transfer of herpes simplex thymidine kinase gene into glioma cells causes targeting of gancyclovir cytotoxic effect. Neurol Med Chir (Tokyo). 1994 June;34(6):339–44. PMID: 7523964; UI: 95022006; Kircheis R, Kichler A, Wallner G, Kursa M, Ogris M, Felzmann T, Buchberger M, Wagner E. Coupling of cell-binding ligands to polyethylenimine for targeted gene delivery. Gene Ther. 1997 May;4(5):409–18. PMID: 9274717; UI: 97420213; Wadhwa M S, Collard W T, Adami R C, McKenzie D L, Rice K G. Peptidemediated gene delivery: influence of peptide structure on gene expression. Bioconjug Chem. 1997 January–February;8(1):81–8. PMID: 9026040; UI: 97178650; Gewirtz A M, Stein C A, Glazer P M. Facilitating oligonucleotide delivery: helping antisense deliver on its promise. Proc Natl Acad Sci U S A. 1996 Apr. 16;93(8):3161–3. Review. No abstract available. PMID: 8622906; UI: 96194935; Zeigler S T, Kerby J D, Curiel D T, Diethelm A G, Thompson J A.

Molecular conjugate-mediated gene transfer into isolated human kidneys. Transplantation. 1996 Mar. 15;61(5):812–7. PMID: 8607188; UI: 96179060; Ledley F D. Nonviral gene therapy: the promise of genes as pharmaceutical products. Hum Gene Ther. 1995 September;6(9):1129–44. Review. PMID: 8527471; UI: 96064111; Boussif O, Lezoualc'h F, Zanta M A, Mergny M D, Scherman D, Demeneix B, Behr J P. A versatile vector for gene and oligonucleotide transfer into cells in culture and in vivo: polyethylenimine. Proc Natl Acad Sci U S A. 1995 Aug. 1;92(16):7297–301. PMID: 7638184; UI: 95365355; Wadhwa M S, Knoell D L, Young A P, Rice K G. Targeted gene delivery with a low molecular weight glycopeptide carrier. Bioconjug Chem. 1995 May–June;6(3):283–91.

PMID: 7632800; UI: 95359276; Martinez-Fong D, Mullersman J E, Purchio A F, Armendariz-Borunda J, Martinez-Hemandez A. Nonenzymatic glycosylation of poly-L-lysine: a new tool for targeted gene delivery. Hepatology. 1994 December;20(6): 1602–8. PMID: 7982661; UI: 95073709; Ledley F D. Non-viral gene therapy. Curr Opin Biotechnol. 1994 December;5(6):626–36. Review. PMID: 7765746; UI: 95143626; Merwin J R, Noell G S, Thomas W L, Chiou H C, DeRome M E, McKee T D, Spitalny G L, Findeis M A. Targeted delivery of DNA using YEE(GalNAcAH)3, a synthetic glycopeptide ligand for the asialoglycoprotein receptor. Bioconjug Chem. 1994 November–December;5(6):612–20. PMID: 7873664; and UI: 95178615; Wu G Y, Wu C H. Evidence for targeted gene delivery to Hep G2 hepatoma cells in vitro. Biochemistry. 1988 Feb. 9;27(3):887–92. PMID: 2835080; UI: 88209440.

In one particular embodiment of the present invention, the method defined above also comprises a step for the production or culture of particles containing organic molecules to be introduced in target cells. This may for example be especially advantageous in the case where the particles are some kind of rapidly degrading biomolecules, such as retroviruses. Accordingly, the method may also involve a step prior to the step of introducing organic molecules into target cells, comprising the culture of virus producing cells. The cells can e.g. be mammalian cells that are capable of producing virus, such as human embryonic kidney cells, for example 293 cells. Retroviral vectors are introduced into cells by either cotransfection with a selectable marker or infection with pseudotyped virus. Such a culture is performed according to any suitable process. Preferably, those cells will secrete the virus into the culture medium, which will constitute the supernatant. For example, retroviral systems are known and generally employ packaging lines which have an integrated defective provirus (the "helper") that expresses all of the genes of the virus but cannot package its own genome due to a deletion of the packaging signal, known as the psi (.psi.) sequence. Thus, the cell line produces empty viral shells. Producer lines can be derived from the packaging lines which, in addition to the helper, contain a viral vector which includes sequences required in cis for replication and packaging of the virus, known as the long terminal repeats (LTRs). The gene of interest can be inserted in the vector and packaged in the viral shells synthesized by the retroviral helper. The recombinant virus can then be isolated and delivered to a subject. (See, e.g., U.S. Pat. No. 5,219,740.)

If requisite, the virus producing cells may be separated from the virus containing liquid flow, or supernatant, in a separate step, e.g. by the use of a filter, before the supernatant contacts the target cells. In a preferred embodiment of the method of the invention, the supernatant is brought to pass through a layer or bed of target cells by use of pumping means, such as a peristaltic pump, but, naturally, any kind of driving device which is capable of transporting the supernatant in the desired direction is of use to this end. In addition or alternatively, a filter may also be used to remove other undesired material from the supernatant, such as toxic or in other ways harmful material. Such material may be the cells producing the biomolecules themselves or other substances resulting from the production step.

In a second aspect the present invention relates to a recombinant cell, which has been transfected by the method according to the invention to harbour one or more foreign organic molecules. As used in this context, the term "foreign" relates to any organic molecule which is not native to the cell wherein such a molecule has been introduced. In one embodiment of this aspect, the organic molecule, which the cell according to the invention harbours, is a retrovirus. The cell is advantageously a stem cell, such as a hematopoietic stem cell. Such a cell can later be useful in therapy, such as gene therapy (for a general reference to gene therapy methods, see e.g. Vigne (1995) Restorative Neurology and Neuroscience 8:35–36), as a diagnostic tool, for experimental purposes, for retroviral marking of hematopoietic stem cells or transfection thereof etc, depending on the target cell and the organic molecule which has been introduced therein.

In a third aspect the present invention relates to a system suitable for the performing a method of introducing at least one organic molecule into one or more target cells, which comprises a reaction vessel arranged to contain target cells in a solution or suspension; and means for passing a supernatant, which comprises organic molecules, by said target cells.

Most preferably, said means for passage of a supernatant through a collection of fluidized or semi-fluidized target cells comprises appropriate tubing as well as a pumping device and can provide an essentially constant flow through the reaction vessel. In addition, a contact between organic molecules, or particles containing organic molecules, and target cells is provided, which is sufficient to if so required enable exit of the organic molecules from the particles and also entrance thereof into the target cells. In this context, the term "essentially constant flow" should be interpreted as a flow, which is constant over a period of time, which, however, may contain shorter periods of intermittent flow or slightly irregular flow.

In this context, the utilized target cells, the particles comprising the organic molecules as well as the organic molecules themselves are as described in detail above in connection with the method according to the invention.

The present system according to the invention can be arranged for use with any kind of transfer of biological substances to target cells. By using a counter gravitational flow of supernatant, which may be a cell culture media, comprising the organic molecule to be transferred, passing through a matrix consisting of free-floating target cells, the present invention provides levels of transduction/transfection above the levels of conventional techniques. (See e.g. FIG. 4 and FIG. 6). The idea of the reverse flow through transduction (RFTT) according to the invention is to minimize cell stress and to have optimal conditions for organic molecule uptake in order to achieve a maximal viral adsorption or transfection. The present system is made from autoclavable materials and the seeding of the system with cells and organic molecule-containing media (DNA transfection complex, virus etc) can be done through sterile septa. The design of the present system should be done with the demands of clinical experiments in mind. It is well suited for retroviral marking of hematopoietic stem cells or transfection thereof. The system has been in transduction experiments for up to $40 \times 10^6$ cells and can be scaled to the desired size to match the needs of clinical use, such as bone marrow transplantation.

The experimental parameters should be controlled to minimize fluctuations in transduction. The present results, see e.g. FIGS. 4 and 6, indicate a marked increase in transduction increase when using the RFTT system according to the invention as compared to conventional static transduction. As the MOI is lowered, the effect of increased cell/virus adsorption in the RFTT is more pronounced causing an increased transduction efficacy and gene expression. As viral gene delivery is used frequently as a tool in a wide range of clinical protocols, it is increasingly important to minimize the amounts of cytokines and viral supernatants. The results indicate that at least 90% reduction in viral supernatant volume is feasible using the present invention as well as a similar decrease in the amount of cytokines used. The present system is adaptable to different volumes and can be designed as a casette system to minimize the risk of contamination in the transduction procedure.

One embodiment of the present invention is a system adapted for transfer of genetic information using retrovirus as carrier i.e. as the component herein denoted a particle. Retrovirus producing cells can then be cultivated in a suitable growth medium i.e. a supernatant in a vessel which supernatant is pumped through a cell separation filter, which prevents virus producing cells from contaminating the target cells, into the reaction vessel. The flow of the supernatant is low enough to prevent the target cells to be swept away but high enough to permit circulation in the reaction vessel comprising target cells to enable maximum exposure of virus particles to target cells. The producer cells in the supernatant vessel are in a specific embodiment cultivated on microcarriers to allow for maximum retroviral titer in the supernatant. Target cells in the reaction vessel may grow in suspension or on microcarriers. The system is closed therby diminishing the risk of contamination by exogenous agents. The system can also be used for cell-free virus supernatants obviating the need for a cell separation filter. This system also allows for nonviral applications, such as transfections and biomolecule interactions with target cells.

In one preferred embodiment of the invention, a widening on the top of the reactor is provided to slow down the flow of supernatant enough so that no cells can escape.

In one embodiment of the system according to the invention, the reaction vessel is a column. The choice of appropriate size and material thereof is easily made by someone skilled in this field considering the kind of process which is to be performed in the system.

In the most preferred embodiment of the system according to the invention, said means for passage of the supernatant through the target cells provides a direction of the flow, which essentially counteracts the gravitational force, or any suitable multiplicity thereof, of the target cells. Alternatively, the supernatant may counteract a centrifugal force applied on the target cells. In any case, the target cells are preferably free floating in the liquid as in a fluidized bed. In an alternative embodiment, the target cells are immobilized on one or more carriers, such as microcarriers, in which case the system provides a fluidized bed comprised of free floating microcarriers instead of free floating target cells.

In a particular embodiment of the system according to the invention, there are also provided means for recirculation of the supernatant one or more times through the target cells to enhance the efficacy of the process performed therein.

As mentioned above, the system according to the invention may further include means for the production of said particles containing the organic molecules, such as a container, vessel or fermenter suitable for culture of the cells producing organic molecules as defined above, e.g. cells producing retroviruses. Conditions for such a culture are commonly known (see e.g. Sambrook et al., Molecular Cloning A Laboratory Manual, $2^{nd}$ Ed., Vol 1–3, Cold Spring Harbor Laboratory, Cold Spring Harbor, N.Y., 1989; Culture of Animal Cells, A Manual of Basic Technique, third ed., Wiley-Liss, New York, N.Y. (1994)) and may easily be adapted for each case by someone skilled in the art. In some cases, it may be advantageous to remove undesired material resulting from such a production step, in which case the system further comprises means for the separation thereof, such as a filter. Undesired material may e.g. be material which is toxic for the target cells or harmful in later application of target cells harbouring organic molecules.

DETAILED DESCRIPTION OF THE DRAWINGS

FIG. 1 shows an illustrative system (Type I) for performing the method according to the invention. A reaction vessel 1 consists of a cylinder with an inner diameter of 1.5 cm and a height of 12 cm, resulting in a volume of 22 cm$^3$. There are two openings in the bottom of the reaction vessel; one being located directly under the center of the cylinder is where the supernatant enters, and the other opening at 90° angle to the reaction chamber. The last mentioned opening is used to inject and extract target cells. The top part of the reaction vessel has three openings; one for injecting media to fill the reaction vessel before starting the circulation; the second is used to release internal air pressure during filling of the reaction vessel, and the third serves as an outlet for the supernatant after passage through the reaction vessel. In one specific embodiment, the reaction vessel has a bulb (Type II) in the top of the reaction vessel to allow a reduction of the flow. The present system is advantageously also equipped with a cell separation filter 2, which is an autoclaveable and non-protein binding filter. This will stop virus-producing cells from entering the reaction vessel and at the same time allow biocomplexes, such as virus and transfection complexes, to enter the reaction vessel. Means for passage of a supernatant through the target cells is depicted in FIG. 1 as a peristaltic pump 3. The peristaltic pump circulates the supernatant through the system. The flow-rate is set so that the cells will achieve a semi-fluidized bed in the reaction vessel and at the same time for optimal adsorption. A producer vessel 4 for the supernatant comprising particles, which particles are e.g. a cell line which produces virus, is shown as a flat-bottomed glass container. A conventional rubber fitting with three openings block the opening. The supernatant can if desired be brought to recirculates through two of them and the third is used for gas exchange. The system according to the invention may further include a circular movement table 5. Such tables are well known in this field and commercially available. The medium/supernatant or producer vessel 4 is placed on a stirrer table to allow for an equal distribution and homogenous concentration in the medium/supernatant that circulates through the system. The reaction vessel 6 will comprise the bed of target cells fluidized by a supernatant passing from its lowe end to its top in order to fluidize said target cells. A sufficient contact will be provided between the particles contained in said supernatant and said target cells for an organic molecule, such as a nucleic acid e.g. DNA, to exit the particles and enter the target cells.

FIG. 2 illustrates a schematical comparison between (A) a prior art flow-through transduction according to Chuck et al (Chuck A. S., Pålsson B. O. Consistent and high rates of gene transfer can be obtained using flow-through transduction over a wide range of retroviral titers. Human Gene Therapy. 7(6):743–50, 1996 Apr. 10) and (B) reversed flow-through transduction according to the invention. Chuck et al have shown, that by allowing a gentle flow of virus supernatant to pass through cells immobilized on a membrane, transduction can be increased at a wide range of viral concentration. At a viral concentration of 0.01 virus/cell, the increase in transduction efficacy was 40-fold. However, the prior art flow-through transduction exhibits several drawbacks. By reversing the flow of supernatant according to the present invention, the limitations of the flow-through transduction system are avoided, specifically the limitation in cell numbers. Another disadvantage with the flow-through system is that free cells and debris can block the filter. Due to the design of the novel system according to the invention, this cannot happen. This is an especially important advantage in ex vivo gene therapy, where a high number of cells are transduced. The reversed flow provided by the present invention will give the cells an upward frictional drag thus preventing packing of cells. As the skilled in this field will realise, too high a flow-rate will wash over cells in the media-containing vessel, while too low a flow will not recirculate a sufficient amount of particles nor fresh media, and the cells will sediment at the bottom of the reaction vessel. A suitable flow-rate is easily determined by routine experimentation to set suitable values for each system. Thus, optimal conditions will be to achieve a fluidized bed.

Figure 3:
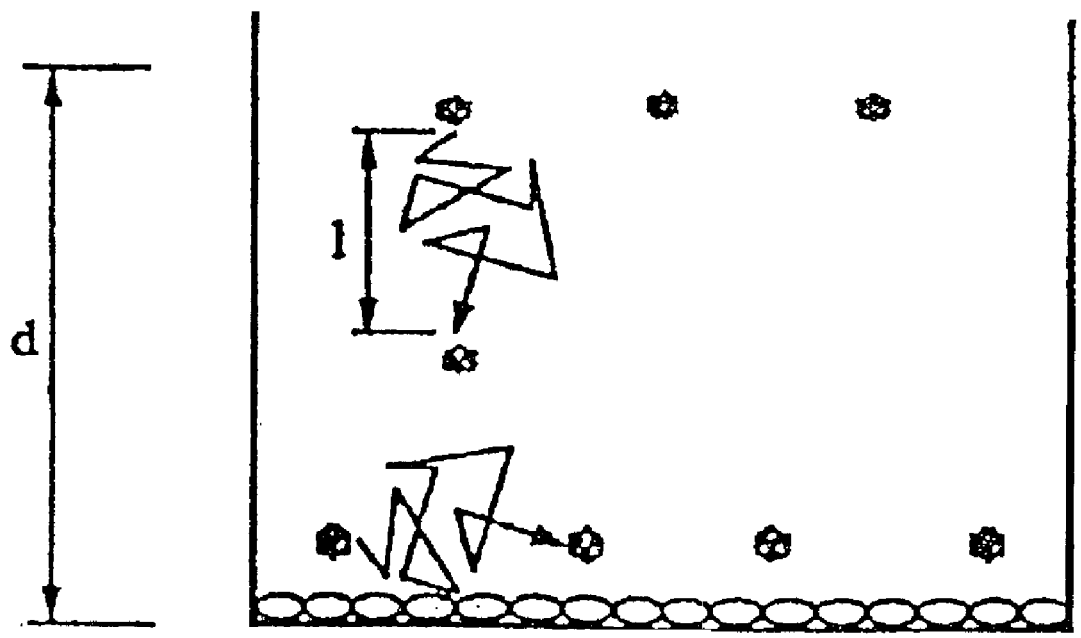
FIG. 3 illustrates the Brownian motion (random motion) of virus.

FIG. 3 illustrates the background for the advantageous performance of the present invention when used with particles in the form of virus. Thus, virus is known to behave like colloidal particles and moves with Brownian motion (Chuck A. S., Clarke M. F., Pålsson B. O. Retroviral infection is limited by Brownian motion. Human Gene Therapy. 7(13):1527–34, 1996 Aug. 20) (random motion) at approximately 480–610 $\mu$m/8 hours in a solution. Considering that the medium surface might be 2–5 mm above the cells at the bottom of the flask, without applying any flow to the system, it will take a long time for the viral particles at the top to reach the cells. Consequently the contact between virus particles and target cells will be insufficient for a useful transfection to occur. This problem is especially apparent for retroviral particles, which are known to have a short halflife. By applying a gentle flow the probability for the viral particles to contact the cells will increase, however without disturbing the required viral-ligand/cellular-receptor interactions.

FIG. 4 shows transduction of murine bone marrow cells with a maloney leukemia virus vector containing the neo selection marker. The moi was 5 and 5 million cells were used in the transduction. The transduced cells were cultured 12–14 days in methylcellulose before scoring for G418 resistant cells. The superior transfection obtained according to the present invention appears clearly from FIG. 4 as the RFTT as compared to the conventional experiment.

Figure 5:
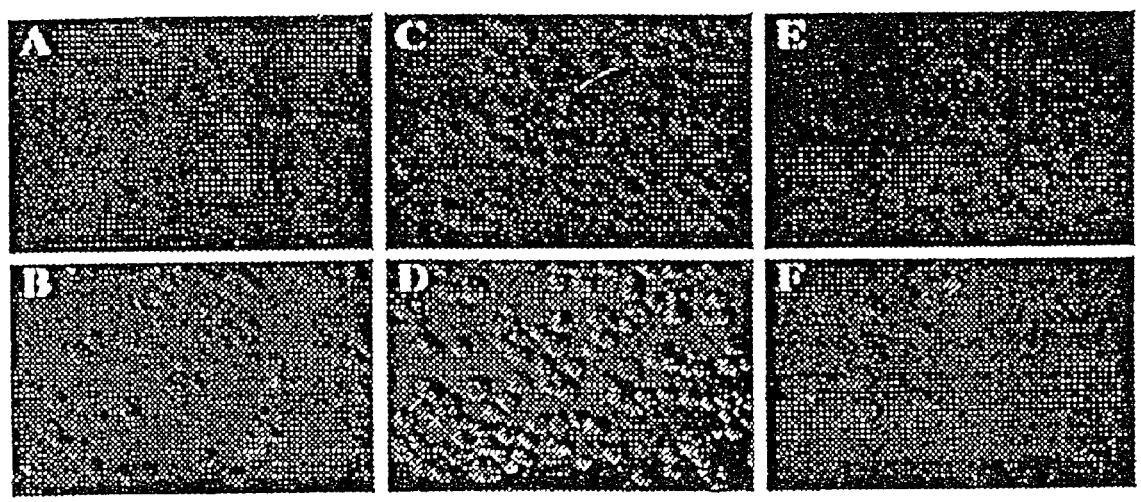
FIG. 5 shows combinatorial images of GFP-adenoviral transduced cells after transduction in the system according to the invention. (A) GFP Negative Jurkat cells; (B) and (C) Conventional transduction experiments; (D) Cells carried over from the reaction vessel to the vessel containing media and supernatant; and (E) and (F) Reaction vessel experiments.

FIG. 5 shows combinatorial images of GFP-adenoviral transduced cells after 48 hours transduction in the system according to the invention. Experiments were made with 48 h conventional transduction with an adenoviral GFP supernatant. The moi was 0.001 and the total amount of RPMI media was 200 ml in the RFTT and flask respectively. (A) GFP Negative Jurkat cells. (B) Conventional transduction experiment according to Chuck et al, Apr. 10, 1996, supra. (C) Conventional transduction experiment according to Chuck et al, Aug. 20, 1996, supra. (D) Cells carried over from the reaction vessel to the vessel containing media and supernatant. (E) Reaction vessel experiment according to Chuck et al, Apr. 10, 1996, supra. (F) Reaction vessel experiment according to Chuck et al, Aug. 20, 1996, supra.

FIG. 6 shows integrated fluorescence measured from the images in FIG. 5. The cells in the vessel seem to have a higher fluorescence and the reason for that can be that it is mainly containing cells that grow rapidly and divide often. Those cells are more metabolically active and hence will produce more GFP protein.

Figure 7:
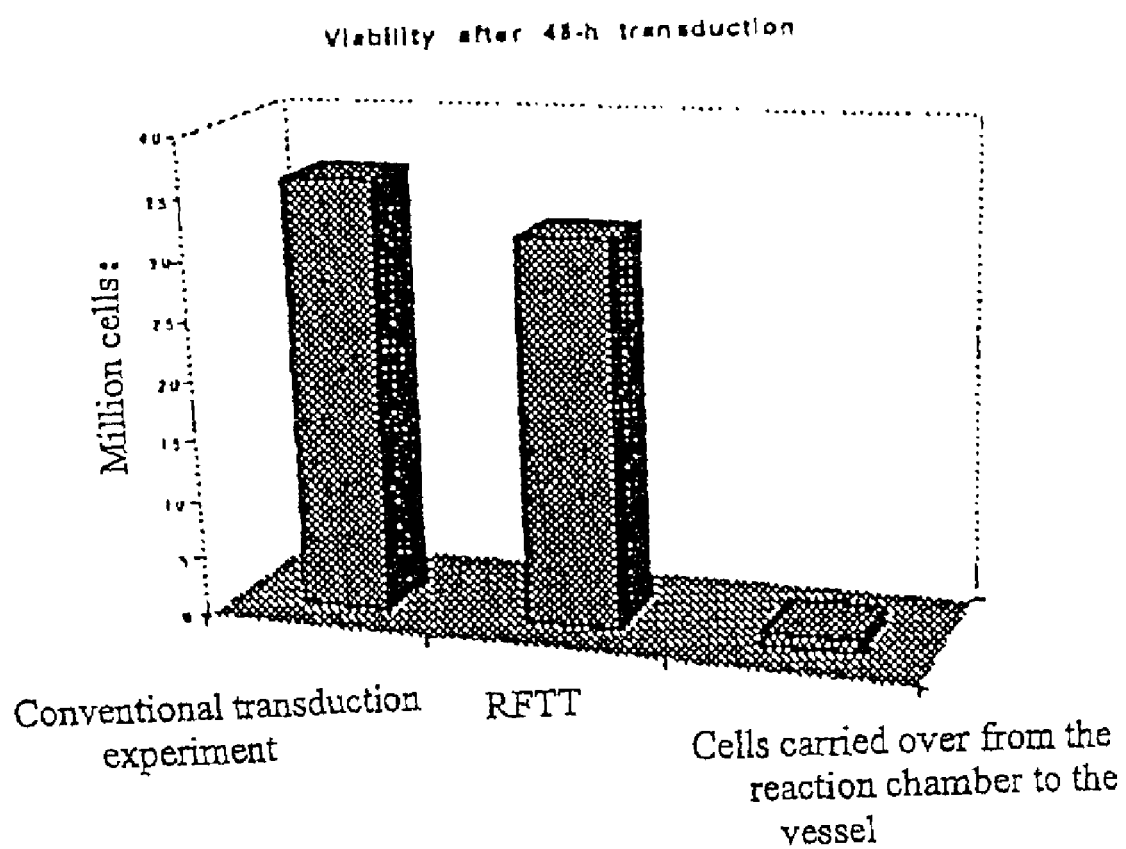
FIG. 7 shows how Jurkat cells were transduced and counted to indicate cell viability in the RFTT system according to the invention in comparison with traditional transduction.

FIG. 7 shows how 13 million Jurkat cells were transduced for 48 h and counted to indicate cell viability in the RFTT system according to the invention in comparison with traditional transduction.

The present invention is more fully described below by examples, which are merely illustrating the invention and which should not be interpreted as limiting the invention in any way. All references below and elsewhere in the present application are hereby included herein by reference.

Experimental

Material and Method

The vessel that contains the supernatant or virus producer cell line is a flat bottomed 25 cm in diameter glass container. The surface does not need to be coated to allow for cell attachment. The opening is blocked by a 4 cm rubber cork with three openings: 1.) Outlet for the supernatant, 2.) Inlet for recirculating supernatant and 3.) A gas exchange filter.

The minimum volume of medium that can be used in this vessel is approximately 150 ml. The outlet is mediated by a glass tube with an internal diameter of 3 mm and a height of 25 cm. This assures that any stray cells detaching from the bottom surface are incapable of entering the circulation, as the gravitational pull is stronger than the flow rate. The supernatant passes through a filter on its way to the reaction chamber. The filter consists of a filter holder with support screens and luer lock fittings. The membrane is a filter with diameter of 5 cm and a pore size of 45 $\mu$m. The membrane is a non-protein binding membrane and it is autoclavable. It is very important that the total assembly is autoclavable to ensure a sterile interior for the transduction. From the filter, the supernatant enters the reaction chamber, where the target cells are. The reaction chamber consists of a cylinder with an internal diameter of 1.5 cm and a height of 12 cm. This gives a volume of 22 $cm^3$. There are two openings in the bottom of the reaction chamber. One is directly under the centre of the cylinder. This is where the supernatant enters. The other opening is at 90° angle to the reaction chamber. This is the opening where the target cells are injected into the reaction chamber and also extracted. The opening is fitted with a autoclavable rubber septum to simplify injection of the target cells. The septum is replaceable, since it is fitted with a screw adapter.

The top of the reaction chamber has three openings:
1. For injecting media to fill the reaction chamber before starting the circulation. This opening is fitted with a rubber septum. 2. To be used to level out internal air pressure during the filling of the reaction chamber. 3. The outlet where the supernatant exits after passing the reaction chamber.

All in/outlets for injecting medium or cells are fitted with Teflon faucets. The outlet tube is connected via a outlet with a vault on it. It leeds straight to the medium container and enables recirculation of the medium/supernatant. The medium/supernatant vessel is placed on a stirrer table to allow for an equal distribution and also a homogenous concentration in the medium/supernatant circulating through the system. The peristaltic pump has a gear that allows for as low a pump rate as 10 ml/h. At this rate the cells within the reaction chamber will not escape it.

EXAMPLE 1
Retrovirus Mediated Gene Transfer with Retroviral Supernatant

The system is put together and autoclaved. The supernatant is aliquoted so that the final concentration is allowing a moi that you choose. In this example, a moi of 5 is used. For a normal human bone marrow transplantation it is usual to use about 100 million, or more, nucleated cells or at least 10 million $CD34^+$ cells. In this case, 10 million $CD34^+$ cells are used. To achieve a moi of 5 50 million cfu are needed. If the supernatant has a concentration of 700 000, 71 ml of the original supernatant will be needed. This is supplemented with appropriate media and cytokines. The media for murine BMC's is Dulbecco's Modified Eagle Medium (DMEM). The cytokines used are IL-3, IL-6 and mSCF. For human cells the same medium and cytokines are used, however, with the difference that the murine cytokines are replaced with the human counterparts.

To fill the system approximately 15 ml of media will be needed, so when making the media, this amount is put a side. First the supernatant to be used is diluted with the freshly made DMEM and supplemented with the cytokines. Then polybrene or another cation of choice is added. In this system, a polybrene concentration of 4 $\mu$g/ml is used. The medium/supernatant container is filled up with 200 ml of supernatant/media mix and put into the incubator together with the rest of the apparatus. To fill the system, the peristaltic pump is turned on and medium/supernatant is pumped until it enters the reaction chamber. After this is done, the reaction chamber is inoculated with the target cells, in this case 10 million $CD34^+$ cells. The cells are injected through the lower opening with the rubber septum. The cells are injected in a volume of 2 ml. After injection of the cell suspension another 2 ml is injected to rinse away any stray cells from the vault and flush them into the reaction chamber. To fill the reaction chamber, 10–12 ml of supernatant/medium mix is slowly injected through the upper septum opening. The 10–12 ml are injected during about 2 minutes or more. Let the cells sediment for 30 minutes before starting the circulation. The circulation should be allowed to continue for as long as the cells are intended to be in the apparatus. For $CD34^+$ cells, the cells are transduced for 48 hours. After the completion of the transduction period, the peristaltic pump is turned off. To extract the cells it is convenient to use a syringe and extract the contents of the reaction chamber. After this is done the peristaltic pump is started again and the flow is turned up to maximum, which in the present case is 35 ml/hour. This will cause all cells still remaining in the region just before the main reaction chamber to be flushed out into the reaction chamber. The reaction chamber is emptied again and the flushing procedure is repeated once more. The resulting 36 ml is centrifuged at 1500 rpm in a standard Sorvall centrifuge for 5 minutes and resuspended in PBS and spun again. After the last wash the cells are resuspended in 1 ml DMEM supplemented with cytokines and 20 $\mu$l is taken out for counting the number of surviving cells. For ordinary methylcellolose cultivation 1000 cells is needed for each 3 cm plate. The methylcellulose is supplemented with cytokines to optimise cell growth. The cells are also supplemented with 0.8 mg G-418/ml to select for cells positive for gene transfer. The assay in done in 5 copies and allowed to grow during 12–14 days and then evaluated for number of G-418 resistant colonies. There are also 3 copies of methylcellulose plates without G-418 to establish the total number of cells capable of forming colonies. The transduction efficacy is given in % resistant colonies v/s the number of colonies growing without G-418.

EXAMPLE 2
Retrovirus Mediated Gene Transfer with Retrovirus Producer Cell Line The system is put together and autoclaved. The medium for murine BMC's is Dulbecco's Modified Eagle Medium, DMEM. The cytokines used are IL-3, IL-6 and mSCF. The same medium is used for human $CD34^+$ cells with the murine cytokines replaced with human counterparts. To fill the system, approximately 15 ml of medium is needed, so when making the media, this amount is put aside. First the media is supplemented with the cytokines. Then polybrene or another cation of choice is added. In this system a polybrene concentration of 4 pg/ml is used. The retrovirus producer cells is irradiated with 400 R and 500 000 cells is resuspended in the medium. The medium/supernatant container is filled up with 200 ml of cell suspension and put in to the incubator together with the rest of the apparatus. The cells are allowed to attach for 5 hours before proceding to fill the system. To fill the system the peristaltic pump is turned on and medium is pumped until it enters the reaction chamber. After this is done the reaction chamber is inoculated with the target cells, in this case 10 million $CD34^+$ cells. The cells are injected through the lower opening covered by the rubber septum. The cells are injected in a volume of 2 ml. After injection of the cell suspension another 2 ml is injected to rinse away any stray cells from the vault and flush them into the reaction chamber. To fill the reaction chamber 10–12 ml of supernatant/medium mix is slowly injected through the upper opening. The 10–12 ml are injected slowly, for about 2 minutes or more. The cells are left to sediment for 30 minutes before starting the circulation. The circulation is allowed to continue for as long as the cells are intended to be in the apparatus. For $CD34^+$ cells, the cells are transduced for +48 hours. After the transduction period is over the peristaltic pump is turned off. To extract the cells it is convenient to use a syringe and extract the contents of the reaction chamber. After this is done the peristaltic pump is started again and the flow is turned up to maximum, which in this case is 35 ml/hour. This will cause all cells still remaining in the region just before the main reaction chamber to be flushed out into the reaction chamber. The reaction chamber is emptied again and the flushing procedure is repeated once more. The resulting 36 ml is centrifuged at 1500 rpm in a standard Sorvall centrifuge for 5 minutes and resuspended in PBS and spun again. After the last wash the cells are resuspended in 1 ml DMEM supplemented with cytokines and 20 $\mu$l is taken out of for counting the number of surviving cells. For ordinary methylcellolose cultivation 1000 cells is needed for each 3 cm plate. The methylcellulose is supplemented with cytokines to optimise cell growth. The cells are also supplemented with 0.8 mg G-418/ml to select for cells positive for gene transfer. The assay in done in 5 copies and allowed to grow for 12–14 days and then evaluated for number of G-418 resistant colonies. There are also 3 copies of methylcellulose plates without G-418 to establish the total number of cells capable of forming colonies. The transduction efficacy is given in % resistant colonies v/s the number of colonies growing without G-418.

EXAMPLE 3
Reverse Flow-through Transduction (RFTT) Apparatus Used for Non-viral Cell Targeting In this example, $CD34^+$ cells are transfected with a pEGFP™ vector using Superfect™.

The system is put together and autoclaved. For the purpose of transfecting cells no filter should be used, since that would disrupt the DNA/superfect aggregates. The media for murine BMC's is Dulbecco's Modified Eagle Medium, DMEM. The cytokines used are IL-3, IL-6 and mSCF. The same media is used for human $CD34^+$ cells with the murine cytokines replaced with human counterparts. If cells are used that demands a different medium this has to be used instead of DMEM. To fill the system approximately 15 ml of media is needed, so when making the media, this amount is put a side. The medium/supernatant container is filled up with 200 ml of medium and put in to the incubator together with the rest of the apparatus. To fill the system the peristaltic pump is turned on and medium is pumped until it starts to enter the reaction chamber. After this is done the reaction chamber is inoculated with the target cells, in this case 10 million $CD34^+$ cells. The cells are injected through the lower opening covered by the rubber septum. The cells are injected in a volume of 2 ml. After injection of the cell suspension another 2 ml is injected to rinse away any stray cells from the vault and flush them into the reaction chamber. To fill the reaction chamber 10–12 ml of supernatant/medium mix is slowly injected through the upper opening. The 10–12 ml are injected slowly, for about 2 minutes or more. The cells are left to sediment for 30 minutes before starting the circulation. Before the circulation is started, the media is first supplemented with the cytokines, the plasmid is mixed with serum free DMEM, 200 µg with 6 ml serum free media. The mixture is added to the media/supernatant container and slowly swirled to allow mixing. After this the circulation is started. The circulation is allowed to continue for as long as the cells are intended to remain in the apparatus. After the transfection period is over the peristaltic pump is stopped. To extract the cells it is convenient to use a syringe and extract the contents of the reaction chamber. After this is done the peristaltic pump is started again and the flow is turned up to maximum in this case 35 ml/hour. This will cause all cells still remaining in the region just before the main reaction chamber to be flushed out into the reaction chamber. The reaction chamber is emptied again and the flushing procedure is repeated once more. The resulting 36 ml is centrifuged at 1500 rpm in a standard Sorvall centrifuge for 5 minutes and resuspended in PBS and spun again. After the last wash, the cells are resuspended in 1 ml DMEM supplemented with cytokines and 20 µl is taken out for counting the number of surviving cells. For ordinary methylcellulose cultivation 1000 cells is needed for each 3 cm plate. The methylcellulose is supplemented with cytokines to optimize cell growth. The cells are also supplemented with 0.8 mg G-418/ml to select for cells positive for gene transfer. The assay is done in 5 copies and allowed to grow for 72 hours to allow for maximum EGFP expression. There are also 3 copies of methylcellulose plates without G-418 to establish the total number of cells and assessing autofluorecence. The transfection efficacy is given in % green cells v/s the number of negative cells.

EXAMPLE 4
A System According to the Invention

The idea of the reverse flow through transduction (RFTT) is to expose the cells under minimal stress to the biomolecules and in an optimal way to allow for either viral adsorption or transfection to take place. The system is made from autoclavable material and the seeding of the system with cells and supernatant comprising particles is performed-through sterile septa well known in this field. The present system fulfills the conventional clinical demands on closed and sterile compartments. It is well suited for clinical trials with for example retroviral marking of hematopoietic stem cells (see FIGS. 1 and 2).

The Vessel that Contains the Supernatant

The supernatant vessel 4 wherein the particles (e.g a virus producer cell line) comprising organic molecules are present is here a flat-bottomed glass container with a diameter of 25 cm. The minimum volume of medium that can be used in the vessel will then be approximately 150 ml. The surface thereof does not need to be coated to allow for cell attachment. A rubber cork with three openings blocks the opening. One outlet is for the supernatant. Another serves as an inlet for recirculating supernatant. The third one is for gas exchange. The supernatant vessel is placed on a conventional stirrer table 5 to allow for an equal distribution and homogenous concentration in the supernatant that will circulate through the system.

Flow of the Supernatant

A peristaltic pump (Fill Master TYPE 251 manufactured by DELTA SCIENTIFIC MEDICAL) will provide circulation of the supernatant through the system. A glass tube with an inner diameter of 3 mm and a height of 25 cm is arranged for passage of the supernatant before it leaves the supernatant vessel 4. The system is adapted for maintaining a flow-rate that is lower than the gravitational force to enable prevention of stray cells detaching from the bottom surface from entering the circulation. Further, an autoclaveable and non-protein binding filter is arranged for the supernatant to pass through on its way to the reaction chamber.

The Reaction Vessel

The reaction vessel consists of a cylinder with an inner diameter of 1.5 cm and a height of 12 cm. This gives a volume of $\approx 22$ $cm^3$. Two openings have been provided in the bottom of the reaction vessel. One has been arranged directly under the center of the cylinder is where the supernatant enters, while the other has been arranged at a 90° angle to the reaction chamber for injection and extraction of the target cells. The top part of the reaction vessel is provided with three openings. One has been arranged for injecting media to fill the reaction chamber before starting the circulation. The second has been arranged to allow release of internal air pressure during filling of the reaction chamber. The third will serve as an outlet for the supernatant after passage thereof through the reaction vessel.

EXAMPLE 5
A Modified System According to the Invention for Dividing Cells

Depending on the cell type it can be necessary to allow cells of a variety of sizes to be retained within the reaction chamber. Thus, the present example shows a system especially adapted for dividing cells that are temporarily of such a small size that the control of the flow alone cannot control the retention of them in the reaction chamber of the type described in Example 4 above. Thus, the present system is arranged with a second-generation reaction vessel to be used when the flow rate tend to carry the cells away. This has been accomplished by a widening of the reaction chamber at the top, which drastically decreases the flow rate. This modification is capable of retaining even the smallest cells in the reaction chamber.

What is claimed is:

1. A method of introducing at least one nucleic acid into one or more target cells, with the passage of a supernatant, wherein nucleic acids are originally maintained, passed through a collection of target cells, said method comprising the steps of a) providing isolated target cells in a reaction vessel, wherein said target cells are capable of allowing entrance of or actively take up nucleic acids;

b) providing a supernatant comprising nucleic acids;

c) contacting the nucleic acids with the target cells by passing the supernatant through a reaction vessel so as to provide a fluidized or semi-fluidized bed of target cells in the reaction vessel, wherein the flow of supernatant through the reaction vessel is controlled to provide essentially constant conditions in the reaction vessel allowing a sufficient contact area and time to enable transfer of nucleic acids from the supernatant into target cells.

2. The method according to claim 1, wherein said nucleic acid is DNA.

3. The method according to claim 1, wherein said nucleic acid is RNA.

4. The method according to claim 1, wherein the nucleic acids prior to step c) have been conjugated to a ligand and the target cells express a receptor for said ligand.

5. The method according to claim 1, wherein the nucleic acids are originally maintained within particles in the supernatant.

6. The method according to claim 5, wherein the particles are capable of interaction with the surface of a target cell.

7. The method according to claim 5, wherein said particles are virus.

8. The method according to claim 5, wherein said particles are retrovirus.

9. The method according to claim 5, which further comprises a step for the production of the particles.

10. The method according to claim 5, which further comprises a step for producing the particles in a virus-producing cell line.

11. The method according to claim 1, which further comprises a step for separation of undesired material from the supernatant, wherein said undesired material is selected from the group consisting of cells producing organic molecules and particles comprising organic molecules.

12. The method according to claim 1, which further comprises a step wherein a sample of target cells is withdrawn and analyzed as regard to whether or not nucleic acids have been introduced therein, and, if required, the value of the flow rate through the vessel is reset to adapt the efficacy of transfer of nucleic acids into target cells.

13. The method according to claim 1, wherein a direction of the supernatant is provided, which essentially counteracts the gravitational force of the target cells.

14. The method according to claim 1, wherein a direction of the supernatant is provided, which essentially counteracts a force applied on the target cells.

15. The method according to claim 14, wherein the force applied on the target cells is a centrifugal force.

16. The method according to claim 1, wherein the supernatant is passed more than one time through the target cells.

* * * * *